United States Patent [19]

Champion et al.

[11] Patent Number: 5,247,078

[45] Date of Patent: Sep. 21, 1993

[54] SYNTHESIS OF DIAZA CROWN ETHERS

[75] Inventors: Donald H. Champion, Pflugerville; George P. Speranza; Terry L. Renken, both of Austin, all of Tex.

[73] Assignee: Texaco Chemical Company, White Plains, N.Y.

[21] Appl. No.: 694,706

[22] Filed: May 2, 1991

[51] Int. Cl.$^5$ .............................................. C07D 267/22
[52] U.S. Cl. ..................................... 540/467; 564/505
[58] Field of Search ........................................ 540/467

[56]        References Cited

U.S. PATENT DOCUMENTS 4,864,062  9/1989  Saito et al. ......................... 564/512
4,906,783  3/1990  Smiley ............................... 564/492

OTHER PUBLICATIONS

A. P. King, et al., "Secondary Amines from Trifluoroacetamides," *Journal of Organic Chemistry*, vol. 39, No. 9, 1974, pp. 1315–1316.

V. J. Gatto, et al., "4,13-Diaza-18-Crown-6 (1,4,10,13-Tetraoxa-7,16-diazacyclooctadecane)," *Organic Synthesis*, vol. 68, 1989, pp. 227–233.

K. E. Krakowiak, et al., "Synthesis of Aza-Crown Ethers," *Chemical Reviews*, vol. 89, No. 4, 1989, pp. 929–972.

*Primary Examiner*—Thurman K. Page
*Assistant Examiner*—Jyothsna Venkat
*Attorney, Agent, or Firm*—James L. Bailey; Kenneth R. Priem; David L. Mossman

[57]            ABSTRACT

Poly(ethyleneoxy)amines, such as those having the structure:

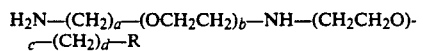

where a and d are independently 2 to 3; b and c are independently 1 to 4 and R is —OH or —NH$_2$, may be reacted over a transition metal catalyst such as one containing nickel to produce diaza crown ethers, such as, for example 4,13-diaza-18-crown-6. If the poly(ethyleneoxy)amine is a diamine having a hydroxyl group of the above formula, the reaction may produce the corresponding triamine in the presence of ammonia. These triamines also readily form diaza crown ethers at near complete conversions simply from nickel, platinum, and palladium metal catalysts alone or with other transition metals such as copper and/or chromium. The process avoids tedious, multiple step procedures and the high dilutions that accompany prior diaza crown ether preparations.

17 Claims, No Drawings

SYNTHESIS OF DIAZA CROWN ETHERS

FIELD OF THE INVENTION

The invention relates to the synthesis of diaza crown ethers and, in one aspect, more particularly relates to the catalytic cyclization of poly(oxyethylene) ether amines to produce diaza crown ethers.

BACKGROUND OF THE INVENTION

Diaza crown ethers are well known materials useful as chelating agents for selective binding and extraction of cations and as antioxidants. A number of other uses are recited in the recent review article by K. E. Krakowiak, et al., "Synthesis of Aza-Crown Ethers," *Chemical Reviews*, Vol. 89, No. 4, 1989, pp. 929–972, 944, including use as key intermediates in the synthesis of cryptands and other N-substituted ligands.

Unfortunately, previous routes to producing the diaza crown ethers, for example the diaza-18-crown-6, are very tedious and expensive, as outlined in the K. E. Krakowiak, et al. article. This publication notes that diaza crown ethers can be prepared by several different routes, for example, reacting 1,2-bis(2-haloethoxy)ethane or triethylene glycol ditosylates with triethylene glycol diamine or bis(tosylamides) followed by removal of the pendant tosyl groups, if required. Another route concerns reacting a primary amine with a 1,2-bis(2-haloethoxy)ethane followed by removal of the pendant alkyl groups; or reacting triethylene glycol diamine with triglycolyl dichloride. A number of other methods are described.

V. J. Gatto, et al. in "4,13-Diaza-18-Crown-6 (1,4,10,13-Tetraoxa-7,16-diazacyclooctadecane)," *Organic Synthesis*, Vol. 68, 1989, pp. 227–233, teach the preparation of the title compound by a three-step procedure that might be considered the standard preparation for these materials. First, benzylamine is reacted with 1,2-bis(2-chloroethoxy)ethane to produce 1,10-dibenzyl-4,7-dioxa-1,10-diazadecane. The product of the first step is then reacted in the presence of 1,2-bis(2-iodoethoxy)ethane, anhydrous sodium carbonate and sodium iodide in acetonitrile to give N,N'-dibenzyl-4,13-diaza-18-crown-6 in the second step. The phenyl groups of the second step product are then removed in a third, hydrogenation step over a palladium catalyst on a carbon support.

The first reference for the preparation of hexaethylene glycol triamine (3,6,12,15-tetraoxa-9-azaheptadecane-1,17-diamine), which is used in the invention herein, is by A. P. King, et al., "Secondary Amines from Trifluoroacetamides," *Journal of Organic Chemistry*, Vol. 39, No. 9, 1974, pp. 1315–1316. It was prepared, along with other compounds including a small amount of 4,13-diaza-18-crown-6, by reaction of 1,8-dichloro-3,6-dioxaoctane and ammonia.

Somewhat related are U.S. Pat. Nos. 4,864,062 and 4,906,783 which produce linear, rather than cyclic amines. For example, a process for producing dioctamethylene triamine is disclosed in U.S. Pat. No. 4,864,062 which comprises dimerizing octamethylene diamine in the presence of a zeolite catalyst represented by the formula: $Na_2O \cdot xSiO_2 \cdot yAl_2O_3$ where x and y are so selected that the molar ratio of $Na_2O$ to $Al_2O_3$ is in the range of 0.02 to 0.05 and the molar ratio of $SiO_2$ to $Al_2O_3$ is in the range of 1 to 10. U.S. Pat. No. 4,906,783 describes the preparation of bis(hexamethylene)triamine from 6-aminohexanenitrile by catalytically preparing di(5-cyanopentyl)amine, followed by hydrogenation using a nitrile hydrogenation catalyst. The first reaction uses at least one metal selected from the class consisting of palladium, platinum, rhodium and ruthenium. The second reaction uses a nitrile hydrogenation catalyst such as Raney cobalt, Raney nickel, supported cobalt, supported nickel and iron oxide.

As may be seen by reviewing the above-noted preparations, diaza crown ethers prepared by conventional methods often require more than one step, high dilution conditions and more than one reagent. All of these considerations increase the cost of the produced crown ethers. It would be desirable if diaza crown ethers could be prepared by a one-step procedure which did not require high dilution.

SUMMARY OF THE INVENTION

Accordingly, it is an object of the present invention to provide a simplified one- or two-step procedures for synthesizing diaza crown ethers.

It is another object of the present invention to provide a method for the preparation of diaza crown ethers that did not require high dilutions.

Another object of the invention is to provide a process for preparing diaza crown ethers from bottoms products that are otherwise considered waste materials.

In carrying out these and other objects of the invention, there is provided, in one form, a process for producing a diaza crown ether by reacting a poly(ethyleneoxy)amine in the presence of a metal catalyst selected from the group consisting of nickel, platinum, palladium and mixtures thereof.

DETAILED DESCRIPTION OF THE INVENTION

It has been discovered that poly(oxyethylene)ether amines may be cyclized over suitable catalysts to give diaza crown ethers. It has been additionally discovered that residues or bottoms products obtained in the manufacture of triethylene glycol diamine (TEGDA) may be upgraded and used to produce the diaza crown ethers. TEGDA is a valuable chemical for the modification of nylon fibers and is also useful as an epoxy curing agent; it is prepared by Texaco Chemical Company by aminating triethylene glycol and sold under the trade name JEFFAMINE® EDR-148 amine. Higher boiling products are also produced in the process.

Bottoms products from any process will vary somewhat, and thus are difficult to define with precision. Bottoms products from the preparation of TEGDA by the reduction of triethylene glycol with ammonia will vary depending upon the temperature and pressure which they are subjected to. Some of the bottoms products, which could be taken overhead, include triethylene glycol monoamine, TEGDA itself, and condensation products having structures such as the following:

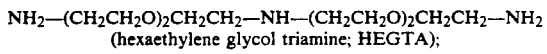
(hexaethylene glycol triamine; HEGTA);

and

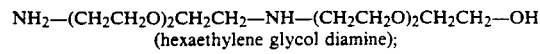
(hexaethylene glycol diamine);

It has been discovered that the value of these bottoms products may be upgraded by further aminating the hydroxyl containing materials such as hexaethylene glycol diamine in the presence of a metal catalyst containing nickel and optionally another transition metal. For example, the hexamethylene glycol diamine is further animated to HEGTA according to reaction (I):

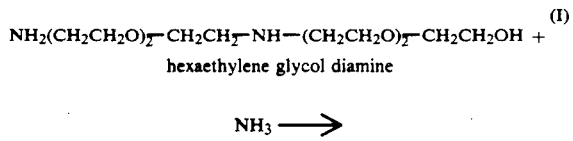

hexaethylene glycol diamine $$NH_3 \longrightarrow$$

$$NH_2(CH_2CH_2O)_2-CH_2CH_2-NH-(CH_2CH_2O)_2-CH_2CH_2NH_2$$

hexaethylene glycol triamine

Suitable catalysts for this reaction include, but are not limited to Raney nickel and nickel catalysts containing copper, chromium, manganese, etc. which are described in U.S. Pat. No. 3,152,998, incorporated by reference herein. The reaction may be conducted at a temperature in the range of about 170° to about 250° C. and a pressure from atmospheric to 300 atm. Preferably, in one aspect of the invention, the reaction is conducted in the range of about 180° to 230° C. and from about 65 to 200 atm.

The analysis of typical residues obtained in the TEGDA process are described in Table I in run 6454-15-0. When such residues were treated with ammonia and hydrogen and passed over a nickel-chrome-copper catalyst described in U.S. Pat. No. 3,152,998 at various temperatures, the results varied as shown in Table I. The efficiency of converting the hydroxyl groups to amine groups reached a maximum at temperatures between 195° and 205° C. (Examples 5 and 6), which is considered an especially preferred range. The products made at 200° C. were carefully fractionated and analyzed. The results are shown in Table II along with results from unaminated residues. As can be seen from the Table, most of the triethylene glycol has been converted to triethylene glycol diamine and the hexaethylene glycol diamine has been converted to hexaethylene glycol triamine, as shown in equation (I) above.

A most interesting aspect was that the concentration of diaza-18-crown-6 increased 880% or by nearly an order of magnitude. The concentration was increased to such an extent that it made isolation of this diaza crown ether relatively simple even at this point.

TABLE I

| Amination of Residues Obtained in Triethylene Glycol Diamine Process | | | | | | |
|---|---|---|---|---|---|---|
| Example | 1 | 2 | 3 | 4 | 5 | 6 |
| Sample No. 6454-15- | 0 | 1 | 2 | 3 | 4 | 5 |
| Temperature, °C. | — | 185 | 190 | 195 | 200 | 205 |
| Analysis: | | | | | | |
| Acetylatables, meq/g | 9.67 | 9.88 | 9.8 | 9.58 | 9.34 | 9.04 |
| Total amine, meq/g | 7.637 | 9.367 | 9.542 | 9.547 | 9.432 | 9.288 |
| Primary amine, meq/g | 4.049 | 5.945 | 6.096 | 5.99 | 5.951 | 4.248 |
| Second. amine, meq/g | 3.499 | 3.33 | 3.303 | 3.324 | 3.141 | 4.526 |
| Tertiary amine, meq/g | 0.089 | 0.092 | 0.143 | 0.233 | 0.34 | 0.514 |
| Hydroxyl groups, meq/g | 2.122 | 0.605 | 0.401 | 0.266 | 0.248 | 0.266 |
| Water, wt. % | 0.251 | 0.753 | 0.83 | 0.72 | 0.99 | 0.84 |
| Total Amine × 100 (Acet. + Tert. am.) | 78.3 | 93.9 | 96 | 97.3 | 97.4 | 97.2 |

TABLE II

| Products in Triethylene Glycol Diamine Residues Before and After Amination | | |
|---|---|---|
| Example | 1 | 4 |
| Contents | Before | After |
| Triethylene glycol diamine, wt. % | — | 20.8 |
| Triethylene glycol monoamine, wt. % | 6.0 | 7.0 |
| Triethylene glycol, wt. % | 36.4 | 2.0 |
| Diaza-18-crown-6 ether, wt. % | 0.025 | 0.22 |
| Hexaethylene glycol triamine, wt. % | 13.6 | 24.0 |
| Hexaethylene glycol diamine, wt. % | 19.4 | 1 |

In other words, it is noted from Table II that the weight percent of hexaethylene glycol triamine (HEGTA) nearly doubled during the amination (from Example 1 to Example 4). As mentioned, HEGTA is particularly useful to be cyclized to give the desirable 4,13-diaza-18-crown-6.

In general the cyclization reaction, sometimes called the second step herein, may be represented schematically by equation (II):

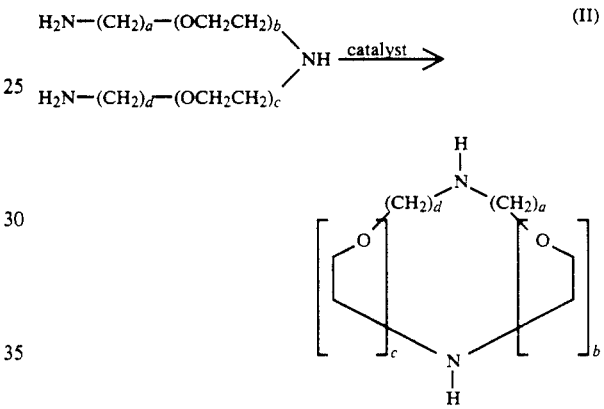

where a and d are independently 2 to 3, and b and c are independently 1 to 4.

The catalysts suitable for this invention include, but are not limited to, supported transition metal catalysts selected from the group of nickel, platinum, palladium and mixtures thereof. Nickel and palladium are particularly preferred, alone or in combination with other transition metals, particularly copper and chromium. For example, the nickel catalysts containing copper, chromium, manganese, etc. which are described in U.S. Pat. No. 3,152,998 were found to be effective. Contrary to the method of U.S. Pat. No. 4,864,062, reaction of HEGTA over a zeolite catalyst gave no diaza crown ether, as will be shown. Additionally, while U.S. Pat. No. 4,906,783 mentions the use of palladium, platinum, rhodium or ruthenium catalysts, it was discovered that ruthenium is ineffective, while platinum is somewhat less selective than palladium or nickel in the reaction of this invention. It is preferred that the metal catalyst is supported. Suitable supports include, but are not limited to, carbon, oxides such as alumina, aluminosilicates, silica and mixtures thereof. It is desirable that from about 0.1 to about 90 wt. % of the catalyst is the active transition metal, preferably from about 0.1 to about 60 wt. %.

The reaction to produce the diaza crown ethers may be conducted at a temperature in the range from about 100° to about 300° C., and preferably from about 150° to about 250° C. The pressure used may range from about atmospheric to about 3000 psig if hydrogen is used.

Relatively lower pressures with a nitrogen sweep facilitates the removal of ammonia, if it is formed in the reaction.

Solvents may be used but are not required. In the event a solvent is employed, it should be inert to the reaction conditions. Suitable solvents include, but are not limited to, triglyme (triethylene glycol dimethyl ether), tetraglyme, other ethers, tertiary alkyl alcohols, tertiary amines, such as bis-morpholino diethylether, and mixtures thereof. Care should be taken in selecting the solvent so that the diaza crown ether may be easily separated therefrom. For example, it was discovered under some conditions that diaza-18-crown-6-ether (DA18C6) was difficult to separate from tetraglyme. Nitrogen may be optionally present, such as by being bubbled through the reaction mixture.

The present diaza crown ether synthesis method does not require high dilution and simply involves heating the amine over a catalyst optionally in the presence of a solvent. The invention will be further illustrated by the following examples which are not intended to limit the scope of the invention.

EXAMPLE 7

Production of DA18C6 from HEGTA

To a 50 ml three-necked flask fitted with a condenser, magnetic stirrer, thermometer and a nitrogen inlet tube were charged 15 ml triglyme and 1.00 g. 0.5% Pd on alumina catalyst. A solution of 10.0 HEGTA in 10 ml triglyme was prepared in an addition funnel and placed on top of the reflux condenser. With nitrogen bubbling through the catalyst slurry, the pot contents were heated to reflux. The solution of HEGTA was then dripped into the pot over 1.3 hours at 213°-217° C. and the addition funnel was rinsed with about 2 ml triglyme which was added to the pot. Further heating of the mixture was done at 213°-217° C. over 17 hours. Gas chromatography analysis (GC) of the product mixture using tetraglyme as an internal standard showed it to contain about 1% by weight of 4,13-diaza-18-crown-6 (DA18C6) and only a small amount of HEGTA.

EXAMPLES 8-20

DA18C6 Production Using Different Catalysts

Example 7 was repeated using several different catalysts. In some cases nitrogen was not bubbled through the reacting mixture. Where a higher reaction temperature was desired, tetraglyme was used as a solvent and the concentration of DA18C6 was not determined. Conditions and results are listed in Table III. In all examples, 10.0 g HEGTA in 27 ml total triglyme was reacted over 1.0 g catalyst unless otherwise indicated.

In Example 15, a zeolite catalyst comparable to that of U.S. Pat. No. 4,864,062 was employed, but no DA18C6 was detected. A ruthenium catalyst comparable to that used in U.S. Pat. No. 4,906,763 was tried in Example 12, but little or no DA18C6 was formed.

TABLE III

Reaction of HEGTA over Various Catalysts

| Ex. | Catalyst | Addition (°C./h) | Stirring (°C./h) | Results |
|---|---|---|---|---|
| 7 | 0.5% Pd/Al$_2$O$_3$ | 217-213/1.3 | 213-217/ca. 17 | Near complete conversion - DA18C6 formed (final concentration about 1%). |
| 8 | (NH$_4$)$_2$Mo$_2$O$_9$[a] | 219-212/1.2[b] | 202-225/21 | Substantially unreacted - no DA18C6 detected. |
| 9 | (NH$_4$)$_2$Mo$_2$O$_9$[a] | 268-254/1.4[b, c] | 258-244/2.0 | Substantially unreacted - no DA18C6 detected. |
| 10 | Ni—Cu—Cr[d] | 250-232/1.5[b, e] | 217-241/3.5 | Complete conversion - DA18C6 formed (final concentration similar to Ex. 7). |
| 11 | Co—Cu—Cr[f] | 220-226/0.8 | 224-229/20 | Substantially unreacted - no DA18C6 detected. |
| 12 | 5% Ru/Al$_2$O$_3$ | 206-210/1.0 | 210-228/18 | Substantially unreacted - little or no DA18C6 detected. |
| 13 | 5% Pt/Al2O3 | 212/ca. 1.5 g | 213-221/ca. 17 | Substantially complete conversion- small amount of DA18C6 formed in low selectivity. |
| 14 | Ni—Cu/alumina[h] | 209-210/0.6 | 210-224/4.0 | Near complete conversion - DA18C6 formed (final concentration about 2%). |
| 15 | Aluminosilicate[i] | 214-210/2.3 | 210-220/18 | Low conversion - no DA18C6 detected. |
| 16 | 5% Pd/C | 170-ca. 190/1.3 | ca. 190-220/20 | Complete conversion - maybe a small amount of DA18C6 formed. |
| 17 | Titanium phosphate | 269-265/1.2 | 265-267/25 | Complete conversion - no DA18C6 detected. |
| 18 | (Ph$_3$P)$_2$Ni(CO)$_2$[a] | 216-222/0.6 | 220-224/22 | Some reaction - no DA18C6 detected. |
| 19 | 50% Ni/alumina[j] | 203-190/1.4 | 180-203/1.3 | Complete conversion - DA18C6 formed (final concentration about 2%). |
| 20 | Raney-Ni[k] | 203-205/1.0 | 205-220/7.6 | Little reaction - no DA18C6 |

TABLE III-continued

Reaction of HEGTA over Various Catalysts Conditions

| Ex. | Catalyst | Addition (°C./h) | Stirring (°C./h) | Results |
|---|---|---|---|---|
| | | | | detected. |

*Catalyst decomposed during reaction.
*No $N_2$ bubbling through.
*1.50 g catalyst, 15.0 g HEGTA, 45 ml tetraglyme.
*Nominally 75% Ni, 22% Cu and 3% Cr based on weight of metals only.
*Reaction in tetraglyme.
*Nominally 75% Co, 22% Cu and 3% Cr based on weight of metals only.
*$N_2$ bubbling failed.
*Ni/Cu 1.5:1; 30% metal oxides.
*Zeolite V ALFOR ® CP300-56 from PQ corporation.
*United Catalysts C-46-7-03.
*About 1.4 g catalyst.

EXAMPLE 21

Reaction using Mixture of Aminated Polyethylene Glycols

A mixture of 301 g aminated polyethylene glycols (containing approximately 21% triethylene glycol diamine, 7% triethylene glycol monoamine, 2% triethylene glycol, 24% hexaethylene glycol triamine and 43% heavier materials) and 15.0 g of Ni-Cu/alumina catalyst was heated at about 200° C. for four hours with nitrogen bubbling through the mixture. It was then flashed as 32.8 g overhead was collected at 85°-187° C. 0.9-1.1 mm. On cooling the distillate, solids formed which were collected and recrystallized from hexanes to give 2.5 g DA18C6. GC analysis indicated 95 Area % DA18C6 (lights free basis).

EXAMPLE 22

In a manner similar to Example 7, 10.0 g hexaethylene glycol diamine, $NH_2$-$(CH_2CH_2O)_2CH_2CH_2$—NH—$(CH_2CH_2O)_2CH_2CH_2$—OH, was reacted over a Ni-Cu-Cr catalyst. The addition was done at 202°-205° C. over 1.7 hours with subsequent stirring at 202°-219° C. for 8.8 hours. GC analysis using tetraglyme as internal standard showed the product to contain about 1% DA18C6.

EXAMPLE 23

To a 300 cc stirred autoclave were charged 5.0 g of a Ni-Cu-Cr catalyst and a solution of 15.0 g HEGTA, 97.5 g triglyme and 2.5 g tetraglyme. The autoclave was purged twice with hydrogen then hydrogen was added to 500 psig. After heating to 225° C. for two hours, a GC sample was taken. Analysis indicated only a small amount of starting material along with about 0.9 wt. % DA18C6. Further reaction for two hours caused the formation of some lighter materials but did not affect the concentration of DA18C6.

EXAMPLE 24

Example 23 was repeated by charging hexaethylene glycol diamine in the place of HEGTA. After two hours of heating, GC analysis indicated about 0.8 wt. % DA18C6. Further heating caused formation of lights, but did not affect the concentration of DA18C6.

Many modifications may be made in the process of this invention without departing from the spirit and scope thereof which are defined only in the appended claims. For example, one skilled in the art may discover that certain reaction conditions or certain catalysts or combinations thereof may give particularly advantageous results.

We claim:

1. A process for producing a diaza crown ether comprising reacting a poly(ethyleneoxy)amine in the presence of a metal catalyst comprising a metal selected from the group consisting of nickel, platinum, palladium and mixtures thereof, where the poly(ethyleneoxy)amine has the structure:

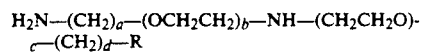

where a and d are independently 2 to 3; b and c are independently 1 to 4 and R is —OH or —$NH_2$.

2. The process of claim 1 where the poly(ethyleneoxy)amine is produced by aminating triethylene glycol diamine bottoms products in the presence of ammonia and a nickel catalyst.

3. The process of claim 1 where the metal catalyst additionally comprises a transition metal selected from the group consisting of copper, chromium and mixtures thereof.

4. The process of claim 1 where the reacting is conducted in the presence of a solvent selected from the group consisting of triglyme, tetraglyme, ethers, tertiary alcohols, tertiary amines, and mixtures thereof, which solvent is inert during the reacting.

5. The process of claim 1 where the metal catalyst is supported on a compound selected from the group consisting of carbon, alumina, aluminosilicate and silica.

6. A process for producing a diaza crown ether comprising reacting a poly(ethyleneoxy)amine of the structure:

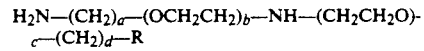

where a and d are independently 2 to 3; b and c are independently 1 to 4 and R is —OH or —$NH_2$, in the presence of a metal catalyst comprising a metal selected from the group consisting of nickel, platinum, palladium and mixtures thereof, where the metal catalyst is supported and consists of from about 0.1 to about 90% of the metal.

7. The process of claim 6 where the metal catalyst additionally comprises a transition metal selected from the group consisting of copper, chromium and mixtures thereof.

8. The process of claim 6 where the metal catalyst is supported on a compound selected from the group consisting of carbon, alumina, aluminosilicate and silica.

9. A process for producing a diaza crown ether comprising the steps of:
    aminating triethylene glycol diamine bottoms products in the presence of ammonia and a metal catalyst comprising nickel to produce a poly(ethyleneoxy)amine where the poly(ethyleneoxy)amine has the structure:

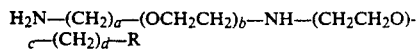
$$H_2N-(CH_2)_a-(OCH_2CH_2)_b-NH-(CH_2CH_2O)_c-(CH_2)_d-R$$

where a and d are independently 2 to 3; b and c are independently 1 to 4 and R is —OH or —NH$_2$;

reacting the poly(ethyleneoxy)amine in the presence of a metal catalyst comprising a metal selected from the group consisting of nickel, platinum, palladium and mixtures thereof.

10. The process of claim 9 where the metal catalyst of the second step is supported and consists of from about 0.1 to about 90% of the metal.

11. The process of claim 9 where the metal catalyst additionally comprises a transition metal selected from the group consisting of copper, chromium and mixtures thereof.

12. The process of claim 9 where the metal catalyst of the second step is supported on a compound selected from the group consisting of carbon, alumina, aluminosilicate and silica.

13. A process for producing a diaza crown ether comprising the steps of:

aminating triethylene glycol diamine bottoms products containing a compound of the formula:

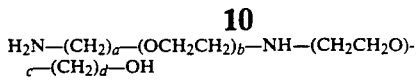
$$H_2N-(CH_2)_a-(OCH_2CH_2)_b-NH-(CH_2CH_2O)_c-(CH_2)_d-OH$$

where a and d are independently 2 to 3 and b and c are independently 1 to 4, in the presence of ammonia and a nickel-copper-chromium catalyst and ammonia to produce a poly(ethyleneoxy)amine of the formula:

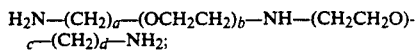
$$H_2N-(CH_2)_a-(OCH_2CH_2)_b-NH-(CH_2CH_2O)_c-(CH_2)_d-NH_2;$$

reacting the poly(ethyleneoxy)amine in the presence of a metal catalyst comprising a metal selected from the group consisting of nickel, palladium and mixtures thereof.

14. The process of claim 13 where the metal catalyst of the second step is supported and consists of from about 0.1 to about 90% of the metal.

15. The process of claim 13 where the metal catalyst of the second step additionally comprises copper and chromium.

16. The process of claim 13 where the second step is conducted in the presence of a solvent selected from the group consisting of triglyme, tetraglyme, ethers, tertiary alcohols, tertiary amines, and mixtures thereof, which solvent is inert during the reacting.

17. The process of claim 13 where the metal catalyst of the second step is supported on a compound selected from the group consisting of carbon, alumina, aluminosilicate and silica.

* * * * *